United States Patent [19]
> Zatloukal et al.

[11] Patent Number: 4,850,373

[45] Date of Patent: Jul. 25, 1989

[54] BIOPSY DEVICE

[75] Inventors: Kurt Zatloukal; Hans P. Dinges, both of Graz, Austria

[73] Assignee: Immuno Aktiengesellschaft fur chemisch-medizinische Produkte, Vienna, Austria

[21] Appl. No.: 173,632

[22] Filed: Mar. 25, 1988

[30] Foreign Application Priority Data

Apr. 13, 1987 [AT] Austria ................................ 914/87

[51] Int. Cl.$^4$ ............................................. A61B 10/00
[52] U.S. Cl. .................................. 128/749; 128/753; 128/754; 604/27; 604/44; 604/264
[58] Field of Search ........................ 128/749, 751–755; 604/22, 27, 35, 43, 44, 45, 264, 272

[56] References Cited

U.S. PATENT DOCUMENTS 4,134,402  1/1979  Mahurkar ............................ 604/272
4,617,940 10/1986  Wang .................................. 128/754

FOREIGN PATENT DOCUMENTS 384165  3/1987  Austria .
 818246  7/1949  Fed. Rep. of Germany .
2643594  4/1977  Fed. Rep. of Germany .
1220646  3/1986  U.S.S.R. .............................. 128/754
1503594  3/1978  United Kingdom .

OTHER PUBLICATIONS

Herbert Thaler, *Leberkrankheiten,* Springer Verlag, 1982, pp. 25–41.
Dtsch.med.Wschr., 92, Jg., No. 39, 29; Sep. 1967, H. Linder, "Grenzen und Gefahren der perkutanen Lebergiopsie . . . ", pp. 1751–1754.
*Luglio,* 1957, vol. XXIX, No. 7, Giorgio Menghini, "Un Effectivo Progresso Nella Tecnica Della Puntura-Biopsia Del Fegato", pp. 756–773.
*The Lancet,* Aug. 25, 1984, S. A. Riley et al, "Percutaneous Liver Biopsy with Plugging of Needle Track: A Safe Method for Use . . . ", p. 436.
*Cancer,* Jun. 15, 1983, vol. 51, R. Douglas McEvoy, "Percutaneous Biopsy of Intrapulmonary Mass Lesions", pp. 2321–2326, American Cancer Society.
Journal of Hepatology, 1986, 2:165–173, F. Piccinino et al, "Complications Following Percutaneous Liver Biopsy".

*Primary Examiner*—Max Hindenburg
*Assistant Examiner*—Randy Citrin
*Attorney, Agent, or Firm*—Burns, Doane, Swecker & Mathis

[57] ABSTRACT

A biopsy device including a two- or multi-lumen biopsy cannula has a biopsy channel of constant cross section over its entire length and at least one application channel. On its proximal end, it is provided with connection facilities for an aspiration device and at least one application device. In order to enable the collection of tissue specimens of an unchanged structure with the most careful handling possible of the tissue and the application of auxiliary substances into the puncture channel without tissue specimens getting into the application cannula and obstructing the same, the cutting edge is formed by an acute-angularly designed end of the biopsy channel wall alone. At least one application channel is formed by a tube eccentrically slipped over the biopsy channel wall. The biopsy channel wall projects out of the tube with its cutting edge and the tube end encloses an obtuse angle with the biopsy channel.

2 Claims, 1 Drawing Sheet

BIOPSY DEVICE

FIELD OF THE INVENTION

The present invention relates to a biopsy device comprising a two or multi-lumen biopsy cannula including a biopsy channel having a constant cross section over its entire length as well as at least one application channel and which is provided, on its proximal end, with connection facilities for an aspiration means and at least one application means, and, on its front end, with a cutting edge.

BACKGROUND OF THE INVENTION

It is known that there exist various bioptic techniques based on the principle of a single-channel needle with aspiration means and/or cutting means, including a trocar or not, to take tissue specimens from animal and human organs. Furthermore, multi-lumen cannulae and needles are known (DE-C - 818 246 and DE-A 2 643 594), which, however, are not suited to take a biopsy and to apply a substance in one operating cycle.

With regard to aspiration biopsy, it is to be noted: The best known aspiration biopsy technique is based on the principle indicated by Menghini (Menghini, G. 1957: Un effettivo progresso nella tecnica della puntura biopsia del fegato. Rass. Fisiopat. clin. Ter. 29, 756). There a hollow needle having an average diameter of 1.4 mm and having a facility for attachment of a syringe is used, by which a negative pressure (suction) is applied upon piercing through the skin and prior to the organ puncture proper. The organ puncture (liver) then is realized with a sustained suction within a second.

With regard to excision biopsy, it is to be noted: Excision biopsy, in principle, is carried out by means of a cannula adequately ground on its front end. The excision means and the lumen of the cannula, during the puncturing procedure, are protected by a stiletto inserted in the lumen of the cannula, which is removed after puncture. It is only then that a cylindrical tissue piece is excised from the punctured organ under suction at a rotating forward movement (e.g., Tru-Cut Needle, Travenol).

With all the bioptic techniques presently in use, complications will have to be taken into account, depending on the type of puncture (as well as the organ to be punctured and on the technique applied) and on the general condition of the patient. The main complications with aspiration biopsy of the liver primarily involve profuse bleeding, bilious peritonitis and pneumothorax (Lindner, H. 1967: Grenzen und Gefahren der perkutanen Leberbiopsie mit der Menghini-Nadel. Dtsch. med. Wschr. 39, 1751; Piccinino F., Sagnelli E., Pasquale G., Guisti G., 1986: Complications following percutaneous liver biopsy. J. Hepatology 2, 165).

Excision biopsies from the lung tissue exhibit a relatively high complication rate due to hemorrhagic incidents and pneumothorax (McEvoy R. D., Begley M. D., Antic R. 1983: Percutaneous Biopsy of Intrapulmonary Mass Lesions. Cancer 51, 2321). Also with kidney biopsies and biopsies of other organs, perfuse bleeding is considered the most important complication.

In order to obviate these complications, it was recommended to subsequently plug the needle track with resorbable material so as to eliminate, in particular, bleeding complications (Riley S. A., Irving H. C., Axon A. T. R., Ellis W. R., Lintott D. J., Losowsky M. S., 1984: Percutaneous Liver Biopsy with Plugging the Needle Track: A Safe Method for Use in Patients with Impaired Coagulation. Lancet, Aug. 25, 1984, 436). Such techniques, however, imply a long residence time of the puncture needle in the organ, which again constitutes a cause of complications, in particular with liver punctures (Thaler H., 1982: Leberbiopsie. Springer-Verlag, Heidelberg - New York).

From Austrian Pat. No. 384,165, a biopsy device of the initially defined kind is known, with which the cannula has a curved partition wall towards the internal limitation of the cannula lumina. Therein, the partition wall does not reach immediately to the front end of the cannula so that the biopsy channel and the application channel communicate in the region of the tip of the cannula. The multi-lumen biopsy device according to Austrian Pat. No. 384,165 enables the collection of tissue and the application of substances plugging the puncture track in coordination with the puncturing procedure in one operating cycle, thus largely shortening the time of intervention.

SUMMARY AND OBJECTS OF THE INVENTION

The present invention has as an object to advance the known biopsy device with a view to enabling the collection of tissue specimens of an unchanged structure with the most careful handling of the tissue possible, and to apply auxiliary substances directly on the site of the puncture without tissue specimens getting into the application cannula, thus obstructing the same.

With a biopsy device of the initially defined kind, this object is achieved according to the invention in that the cutting edge is formed by an acute-angularly designed end of the biopsy channel wall alone and at least one application channel is formed by a tube eccentrically slipped over the biopsy channel wall, the biopsy channel wall projecting out of the tube with its cutting edge and the tube end enclosing an obtuse angle with the biopsy channel wall.

It is of relevance to the careful handling of the tissue sought by the invention when using this biopsy device, that the tissue slides away from the cutting edge at the biopsy channel wall as the biopsy cannula is pierced in and penetrates further inwards, and that the surrounding tissue, upon further penetration, without exerting pressure, merely is displaced by the adequately ground tube end of the application channel without obstructing the application channel.

Preferably, the biopsy channel wall ends at a right angle relative to the longitudinal axis of the biopsy channel.

Preferably, the biopsy channel wall is partially flattened in the cross section such that an application channel is formed between the flattened side of the biopsy channel wall and the tube and that a surface contact exists between the non-flattened side of the biopsy channel wall and the tube.

BRIEF DESCRIPTION OF THE DRAWINGS

The invention will now be explained in more detail by way of one embodiment illustrated in the drawing, wherein.

DETAILED DESCRIPTION OF A PREFERRED EMBODIMENT

Figure 1:
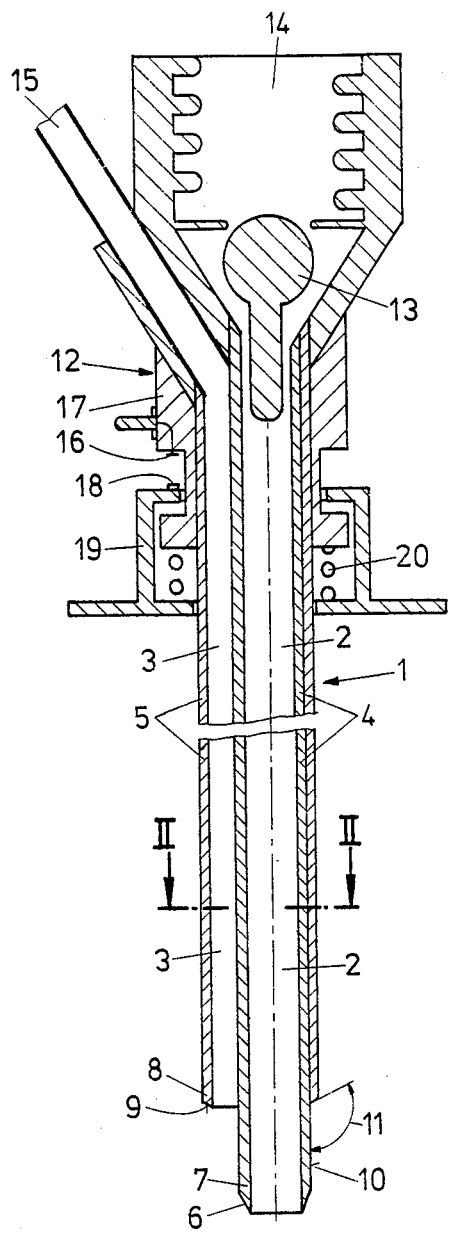
FIG. 1 is a longitudinal section through a biopsy device according to the invention.
Figure 2:
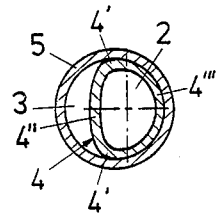
FIG. 2 is a transverse section along line II—II of FIG. 1.

The biopsy device according to the invention comprises a two-lumen biopsy cannula 1, in the following briefly referred to as cannula, including a biopsy channel 2 and an application channel 3. The biopsy channel 2 is formed by a tubular biopsy channel wall 4, having a constant asymmetric cross section over its entire length in the form of a circle flattened on one side. An eccentrically arranged tube 5 having a circular cross section is slipped over the biopsy channel wall 4 under mutual contact, the contacting surface extending approximately over half of the circumferential region of the tube 5. The application channel 3 is delimited by the non-adjacent regions of the tube 5 and by the flattened side 4" of the biopsy channel wall 4, the biopsy channel wall 4, via curvatures 4', verging from the flattened side 4" into the circular arc side 4'" by tangential contact with the wall 5 such that the biopsy channel 2 has no corners or edges affecting the quality of the biopsy.

The biopsy channel wall 4 projects out of the tube 5 with its front end 7 arranged at a right angle to its longitudinal axis of the biopsy channel 2 and having a cutting edge 6 ground at an acute angle. The tube 5 is provided with an end 8 likewisely arranged at a right angle to its longitudinal axis and whose end face 9 encloses an obtuse angle 11 with the external side 10 of the biopsy channel wall, the end 8 of the tube 5 being designed in a substantially less acute angle than the cutting edge 6 of the biopsy channel wall 4.

On the proximal end 12 of the cannula 1, there is disposed a pin 13, which closes the biopsy channel 2 not completely and prevents the tissue specimen from being aspirated into the negative-pressure system to be connected at 14 (e.g., syringe with lock). At reference numeral 15, the facility for attachment of an application system is denoted, whose concept and design (e.g., cone, thread, etc.) may be adapted to the respective requirements (e.g., system under pressure). The limitation of the puncturing depth and the control of the application system are realized by a mechanism provided on the cannula 1, which is composed of a part 17 fastened to the cannula 1 and having one or several contact points 16 as well as of a movable part 19 having one or several counter contact points 18 and being maintained in a starting position by a spring 20, in which position the contact points 16 and the counter contact points 18 are separate from each other. When reaching a certain puncturing depth, the movable part 19, upon contact with the body surface, is moved in the direction towards part 17 until stopped, the contact between the contact points 16 and the counter contact points 18, thus, being closed. The number and disposition of contact and counter contact points may be chosen according to the requirements in terms of application system control. Instead of the electric control system outlined, a mechanical system may be used without altering the principle of the present invention.

Puncturing is effected according to the Menghini technique, with which, upon piercing through the skin, a negative pressure is produced in the biopsy channel 2 by the aid of a lockable syringe attached at point 14. Subsequently, the cannula 1 is further pierced into the tissue (organ) to be punctured. The tissue to be collected at first is excised by the cutting edge 6 of the biopsy channel wall 4 and afterwards slides along the internal side of the biopsy channel wall 4 by further penetrating into the cannula 1 at the same time. Due to the slightly bevelled end 8 of the tube 5, the surrounding tissue merely is displaced, thus avoiding obstruction of the application channel.

Upon contact closure of the two parts 17 and 19, the needle is withdrawn at once. The injection of substances via the application channel 3 (e.g., blood coagulation substances, vasoactive drugs, cytostatics, antibiotics, etc.) is automatically released by the releasing mechanism upon arrival at a predetermined piercing depth.

What we claim is:

1. In a biopsy device of the type including a biopsy cannula, a proximal end and a front end opposite said proximal end, said biopsy cannula comprises:
   a biopsy channel wall defining a biopsy channel of constant cross section over its entire length,
   at least one application channel,
   connection facilities provided on said proximal end of the biopsy channel for connecting the biopsy channel to means for producing a low pressure;
   connection facilities for at least one application means provided on said proximal end of the application channel for applying substances through said application channel, and
   a cutting edge provided on said front end of the biopsy channel wall,
   said biopsy channel wall comprising a first tube and said cutting edge is formed by an acute-angularly designed end of said first tube,
   wherein a second tube is eccentrically arranged over said first tube to form said at least one application channel separate from said biopsy channel,
   said first tube having said cutting edge projecting out of said second tube and said second tube having a front tube end forming an obtuse angle with said first tube.

2. A biopsy device as set forth in claim 1, wherein said first tube is partially flattened in cross section so as to have a flattened side and a non-flattened side, said application channel being formed between said flattened side of said first tube and said second tube and a surface contact existing between said non-flattened side of said first tube and said second tube.

* * * * *